United States Patent [19]

Martin et al.

[11] Patent Number: 4,514,411
[45] Date of Patent: Apr. 30, 1985

[54] SUBSTITUTED 4,10-DIHYDRO-10-OXOTHIENO BENZOXEPINS

[75] Inventors: Lawrence L. Martin, Lebanon; Linda L. Setescak, Somerville, both of N.J.

[73] Assignee: Hoechst-Roussel Pharmaceuticals Inc., Somerville, N.J.

[21] Appl. No.: 639,548

[22] Filed: Aug. 10, 1984

Related U.S. Application Data

[62] Division of Ser. No. 474,218, Mar. 10, 1983, Pat. No. 4,477,465.

[51] Int. Cl.³ .................. A61K 31/42; C07D 495/04
[52] U.S. Cl. .................................... 514/215; 548/237
[58] Field of Search ........................ 548/237; 424/272

[56] References Cited

U.S. PATENT DOCUMENTS 4,025,640 5/1977 McFadden et al. ............... 424/275

OTHER PUBLICATIONS

Aultz et al., J. Med. Chem., vol. 20, (1977), pp. 66-70 and 456-458.
Yoshioka et al., J. Med. Chem., vol. 21, (1978), pp. 633-639.

*Primary Examiner*—Richard L. Raymond
*Attorney, Agent, or Firm*—Jerome Rosenstock

[57] ABSTRACT

This invention relates to substituted 4,10-dihydro-10-oxothieno benzoxepins of the formula,

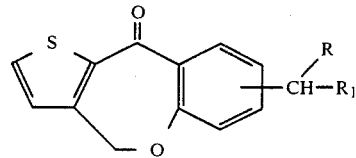

where R is hydrogen and lower alkyl; $R_1$ is

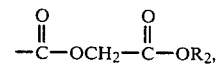

where $R_2$ is hydrogen, lower alkyl and benzyl of the formula

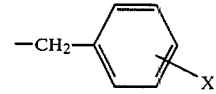

where X is hydrogen, lower alkyl, lower alkoxy, halogen, trifluoromethyl, nitro, and amino;

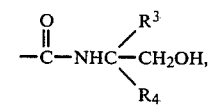

where $R_3$ and $R_4$ are the same or different and are hydrogen and lower alkyl;

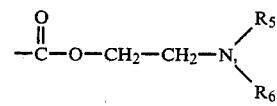

where $R_5$ and $R_6$ are the same or different and are lower alkyl; and the pharmaceutically acceptable acid addition salts thereof.

4 Claims, No Drawings

SUBSTITUTED 4,10-DIHYDRO-10-OXOTHIENO BENZOXEPINS

This is a division of application Ser. No. 474,218 filed Mar. 10, 1983, U.S. Pat. No. 4,477,465.

To the best of our knowledge the compounds of the present invention have not heretofore been described or suggested.

The compounds of the present invention have the general formula,

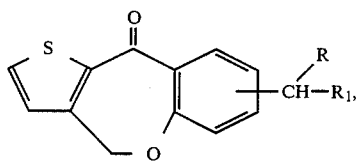

where R is hydrogen and lower alkyl; $R_1$ is

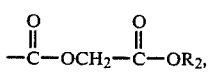

where $R_2$ is hydrogen, lower alkyl and benzyl of the formula

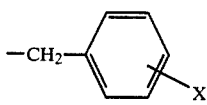

where X is hydrogen, lower alkyl, lower alkoxy, halogen, trifluoromethyl, nitro, and amino; and

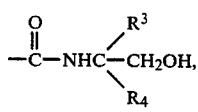

where $R_3$ and $R_4$ are the same or different and are hydrogen and lower alkyl;

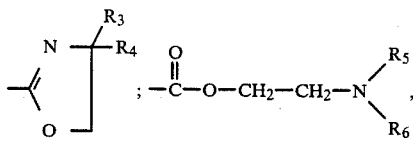

where $R_5$ and $R_6$ are the same or different and are lower alkyl; and the pharmaceutically acceptable acid addition salts thereof.

Particularly preferred compounds of the invention are those of Compound I where R is H or methyl and $R_1$ is

In the above definitions and as used hereinafter, the term "lower" means the group it is describing contains 1 to 6 carbon atoms. The term "alkyl" refers to a straight or branched chain hydrocarbon containing no unsaturation e.g. methyl, ethyl, propyl, tertiary-butyl, isopropyl, etc. The term "alkoxy" refers to a monovalent substituent which consists of an alkyl group linked through an ether oxygen having its free valence bond from the ether oxygen, e.g. methoxy, ethoxy, isopropoxy, butoxy, etc. The term "halogen" refers to a member of the family consisting of fluorine, chlorine, bromine and iodine.

The compounds of the present invention are prepared in the following manner. The substituents R, $R_1$ through $R_6$ and X are as defined above unless indicated otherwise.

A 4,10-dihydro-10-oxothieno[3,2c][1]benzoxepin acetic acid is employed of the formula II,

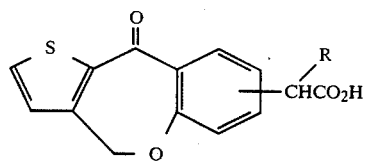

Compounds II are prepared generally in the manner described in U.S. Pat. No. 4,025,640, incorporated hereinto by reference, such as for example in the manner of Example 1 thereof.

Compound II is converted in a conventional manner to an acyl halide of the structural formula III,

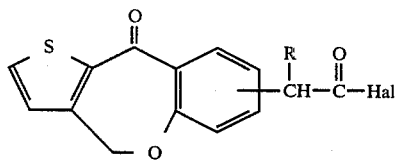

where Hal is a halogen. Typically, such conversion is carried out by reaction with an inorganic halide such as for example, phosphorus trihalide or pentahalide or thionyl chloride.

Compound III is reacted with an amino substituted alcohol of the formula

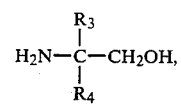

in a suitable inert solvent, e.g. methylene chloride, at a typical temperature of 0° to 25° C., for 0.1 to 12 hours to form a compound of the invention having the structural formula

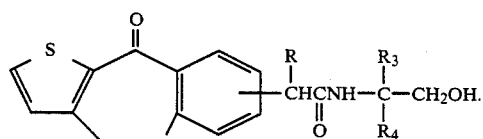

Compound V can be treated with a conventional dehydrating agent, e.g. an acidic dehydrating agent such as thionyl chloride, typically at 0° to 25°, preferrably from 0° to 10° C., for a time period of from 2 to 3 minutes to about 12 hours, to form a 5 membered ring system substituent of a compound of the invention having the structural formula

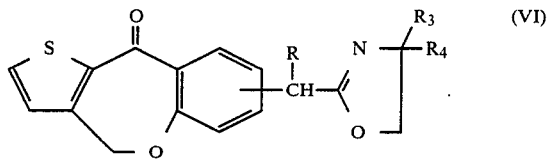

Compound II is reacted under conventional substitution reaction conditions, e.g. in the presence of base, e.g. K₂CO₃, with either an alkyl halo acetate of the formula

or a halosubstituted amine of the formula

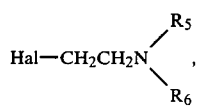

where Hal is a halogen, (VIII), to form a compound of the invention having the structural formula

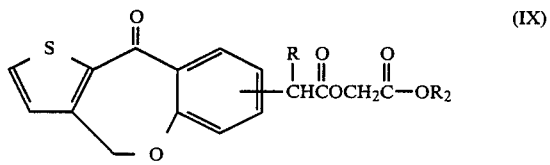

or a compound of the invention having the structural formula

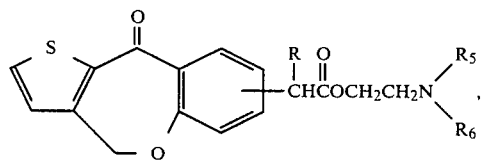

respectively.

The compounds of the present invention are useful as antiinflammatory agents due to their ability to suppress inflammation in mammals. The activity of the compounds is demonstrated in the carrageenin induced rat paw edema antiinflammatory assay [Proc. Soc. Exptl. Biol. Med., III 544 (1962), J. Pharmacol. Exp., 141 (1963)]. Table I below reveals the anti-inflammatory activity of some of the compounds of this invention.

TABLE I

| Compound | Canageenin Paw Edema | |
|---|---|---|
| | % | dose mg/kg (p.o.) |
| 2-(4,10-Dihydro-10-oxothieno[3,2-c][1]benzoxepin-8-yl)methyl-4,4-dimethyloxazoline | 49 | 20 |
| Methyl[4,10-dihydro-10-oxothieno[3,2-c][1]benzoxepin-8-yl)acetoxyacetate | 43 | 20 |

The compounds of the invention compare favorably with the well known antiinflammatory compound phenylbutazone, which, in a similar test, exhibited antiinflammatory activity of a 50% inhibition of edema at a dose of 50 mg/kg (p.o.).

Compounds of the present invention are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table II below reveals the analgesic activity of some of the compounds of this invention.

TABLE II

| Compound | Phenylquinone Writhing ED₅₀ Orally (p.o.) mg/kg |
|---|---|
| 2-(4,10-Dihydro-10-oxothieno[3,2-c][1]benzoxepin-8-yl)methyl-4,4-dimethyloxazoline | 7.22 |
| Methyl(4,10-dihydro-10-oxothieno[3,2-c][1]benzoxepin-8-yl)acetoxyacetate | 1.53 |

The compounds of the invention compare favorably with the well known analgesic compound indomethacin, which, in a similar test exhibited analgesic activity of an ED₅₀ of 0.7 mg/kg (p.o.).

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts or base addition salts, where appropriate, for purposes of stability, convenience of crystallization, increased solubility and the like.

Preferred pharmaceutically acceptable acid addition salts include those derived from inorganic acids such as hydrochloric hydrobromic, sulfuric, nitric, phosphoric, perchloric acids and the like as well as organic acids such as tartaric, citric, succinic, maleic, furmaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the 4,10-dihydro-10-oxothieno benzoxepin derivatives of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the substituted 4,10-dihydro-10-oxothieno benzoxepins of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex;

a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 4,10-dihydro-10-oxothienobenzoxepin derivative of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the 4,10-dihydro-10-oxothienobenzoxepin derivative of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparations can be enclosed in ampules, disposable syringes or multiple dose vails made of glass or plastic.

Examples of the invention include: 2-(4,10-dihydro-10-oxotheno[3,2-c][1]-benzoxepin-7-yl)methyl-4,4-dimethyloxazoline; 4,10-dihydro-N-(1-hydroxy-2-methyl-2-propyl)-10-oxothieno[3,2-c][1]benzoxepin-7-yl acetamide; methyl(4,10-dihydro-10-oxothieno[3,2-c][1]-benzoxepin-7-yl)acetoxyacetate; 4,10-dihydro-10-oxothieno[3,2-c][1]-benzoxepin-8yl-acetic acid; 4,10-dihydro-10-oxothieno[3,2-c][1]-benzoxepin-6yl-acetic acid; 4,10-dihydro-10-oxothieno[3,2-c][1]-benzoxepin-9-acetic acid.

The following examples are for illustrative purposes and are not to be construed as limiting the invention disclosed herein. All temperatures are given in degrees centigrade.

EXAMPLE 1

4,10-Dihydro-N-(1-hydroxy-2-methyl-2-propyl)-10-oxothieno[3,2-c][1]benzoxepin-8-yl acetamide To a warm solution of 20 g (0.07 m) of 4,10-dihydro-10-oxothieno[3,2-c][1]benzoxepin-8-acetic acid in 400 ml of $CH_2Cl_2$, a few drops of dimethylformamide (DMF) was added followed by the dropwise addition of 19.0 g (0.16 m) of $SOCl_2$. The mixture was refluxed 2 hours. The solvents were evaporated giving 18 g of the corresponding acid chloride as a solid, m.p. 89°–93° C. To a solution of 13.35 g (0.15 m) of 2-amino-2-methyl-1-propanol in 50 ml of $CH_2Cl_2$, a solution of 15 g of the resulting corresponding acid chloride in 200 ml of $CH_2Cl_2$ was added dropwise. The mixture was stirred as a precipitate formed and was stirred overnight (about 16 hours). After filtration, the insoluble material was triturated with water and the water insoluble material was collected to give 11.08 g of product. The $CH_2Cl_2$ filtrate was washed with 5% HCl, and 10% NaOH solution, dried ($Na_2SO_4$), filtered and evaporated to give 4.4 g of product. The total product isolated of 4,10-dihydro-N-(1-hydroxy-2-methyl-2-propyl)-10-oxothieno[3,2-c][1]benzoxepin-8-yl acetamide was 15.4 g (87%). A sample of the product was recrystallized from acetonitrile for analysis and testing, m.p. 162°–163° C.

ANALYSIS: Calculated for $C_{18}H_{19}NSO_4$: 62.59%C; 5.54%H; 4.06%N. Found: 62.55%C; 5.51%H; 4.03%N.

EXAMPLE 2

2-(4,10-Dihydro-10-oxothieno[3,2-c][1]benzoxepin-8-yl)methyl-4,4-dimethyl-oxazoline To a suspension of 8.3 g (0.02 m) of 4,10-dihydro-N-(1-hydroxy-2-methyl-2-propyl)-10-oxothieno[3,2-c][1]benzoxepin-8-yl acetamide of Example 1 and 200 ml of methylene chloride, $SOCl_2$ (3.09 g) was added dropwise keeping the temperature at approximately 5° C. The suspended material gradually dissolved. The mixture was stirred overnight (about 16 hours). The organic layer was washed with 10% NaOH, dried ($Na_2SO_4$) and evaporated to give an oil. Trituration with isopropyl ether gave 4.1 g (52%) of 2-(4,10-dihydro-10-oxothieno[3,2-c][1]benzoxepin-8-yl)methyl-4,4-dimethyl-oxazoline, m.p. 85°–87° C.

ANALYSIS: Calculated for $C_{18}H_{17}NO_3S$: 66.03%C; 5.24%H; 4.28%N. Found: 65.73%C; 5.29%H; 4.09%N.

EXAMPLE 3

Methyl(4,10-dihydro-10-oxothieno[3,2-c][1]benzoxepin-8-yl)acetoxyacetate

A mixture of 12.54 g (0.046 m) of 4,10-dihydro-10-oxothieno[3,2-c][1]benzoxepin-8-acetic acid in 100 ml of dimethylformamide (DMF) and 3.18 g (0.033 m) of $K_2CO_3$ was warmed to 60° C. for 1 hour in an atmosphere of nitrogen. To this mixture 7.7 g (0.05 m) of methyl bromoacetate was added dropwise and the mixture was held at 60° C. overnight (about 16 hours). The reaction mixture was poured into water and extracted with ether. The ether extract was washed with 5% $NaHCO_3$ and water, dried over $Na_2SO_4$, filtered and evaporated to give an oil which solidified. Trituration with hexane gave 12.5 g (78%) of methyl(4,10-dihydro-10-oxothieno[3,2-c][1]benzoxepin-8-yl)acetoxyacetate, m.p. 78°–80° C.

ANALYSIS: Calculated for $C_{17}H_{14}SO_6$: 58.95%C; 4.07%H. Found: 59.16%C; 4.18%H.

We claim:

1. The compound which is 2-(4,10-dihydro-10-oxothieno[3,2-c][1]benzoxepin-8-yl)methyl-4,4-dimethyloxazoline or a pharmaceutically acceptable salt thereof.

2. An anti-inflammatory or an analgesic composition which comprises an effective anti-inflammatory or pain alleviating amount of 2-(4,10-dihydro-10-oxothieno[3,2-c][1]benzoxepin-8-yl)-methyl-4,4-dimethyloxazoline or a pharmaceutically acceptable salt thereof.

3. A method of alleviating pain in a mammal which comprises administering to a mammal an effective pain alleviating amount of 2-(4,10-dihydro-10-oxothieno[3,2-C][1]-benzoxepin-8-yl)methyl4,4-dimethyloxazoline or a pharmaceutically acceptable salt thereof.

4. A method of alleviating inflammation in a mammal which comprises administering to a mammal an effective amount of 2-(4,10-dihydro-10-oxothieno[3,2-C][1]-benzoxepin-8-yl)methyl4,4-dimethyloxazoline or a pharmaceutically acceptable salt thereof.

* * * * *